US008853667B2

(12) United States Patent
Jain et al.

(10) Patent No.: US 8,853,667 B2
(45) Date of Patent: Oct. 7, 2014

(54) QUANTUM DOT GATE FETS AND CIRCUITS CONFIGURED AS BIOSENSORS AND GENE SEQUENCERS

(71) Applicant: Faquir C. Jain, Storrs, CT (US)

(72) Inventors: Faquir C. Jain, Storrs, CT (US); Robert A. Croce, Jr., Guilford, CT (US); Anjana Jain, Worcester, CT (US)

( * ) Notice: Subject to any disclaimer, the term of this patent is extended or adjusted under 35 U.S.C. 154(b) by 42 days.

(21) Appl. No.: 13/707,278

(22) Filed: Dec. 6, 2012

(65) Prior Publication Data

US 2013/0140518 A1  Jun. 6, 2013

Related U.S. Application Data

(60) Provisional application No. 61/567,507, filed on Dec. 6, 2011.

(51) Int. Cl.
*H01L 29/06* (2006.01)
*H01L 31/00* (2006.01)
*H01L 29/66* (2006.01)
*B82Y 99/00* (2011.01)

(52) U.S. Cl.
CPC ............... *H01L 29/66* (2013.01); *B82Y 99/00* (2013.01); *H01L 29/0684* (2013.01); *Y10S 977/773* (2013.01)
USPC ............ 257/12; 257/253; 257/414; 438/49; 977/773

(58) Field of Classification Search
None
See application file for complete search history.

(56) References Cited

U.S. PATENT DOCUMENTS

| 8,294,137 | B2 * | 10/2012 | Jain et al. ............... 257/24 |
| 2008/0154101 | A1 * | 6/2008 | Jain et al. ............... 600/309 |
| 2009/0173934 | A1 * | 7/2009 | Jain ........................ 257/20 |
| 2010/0224861 | A1 * | 9/2010 | Jain et al. ............... 257/20 |

OTHER PUBLICATIONS

Jain et al, Spatial Wavefunction-Switched (SWS) InGaAs FETs with II-VI Gate Insulators, Journal of Electronic Materials Aug. 2011, vol. 40, Issue 8, pp. 1717-1726.*

* cited by examiner

*Primary Examiner* — Andres Munoz
(74) *Attorney, Agent, or Firm* — Steven M. McHugh

(57) ABSTRACT

Quantum dot (QD) gate FETs and the use of quantum dot (QD) gate FETs for the purpose of sensing analytes and proteins is disclosed and described. Analytes, proteins, miR-NAs, and DNAs functionalized to the QDs change the charge density in the gate and hence the current-voltage characteristics. In one embodiment, QD-FETs, such as 3-state configurations, the binding of chemical and biological species change the drain current-gate voltage characteristics resulting in detection. In one embodiment, DNA sensing is done by its binding to an existing reference DNA functionalized on to quantum dots which are located in the gate region of the FET.

5 Claims, 15 Drawing Sheets

Carbon nanotube FET configured as an immunoglobulin E (IgE) antibody sensor

Prior Art

Au gated p-FET used for DNA sensing

Prior Art

Organic Redox-based glucose sensor utilizing a PEDOT channel

Prior Art

Floating gate FET used for pH sensing in DNA hybridization applications

Quantum dot gate FET for DNA, RNA, MicroRNA sensing and sequencing applications and (inset) silane components for the chemical modification of the QDs.

Quantum dot gate FET used in affinity-type biomolecule sensing applications

Drain Current ID-Drain Voltage VD characteristics of Si/SiO$_x$ Quantum dot gate FET used for Thrombin sensing via ssDNA Thrombin aptamers functionalized to the quantum dots Quantum dot gate FET coated with glucose axidase for glucose sensing in a redox based configuration Quantum dot gate FET used for pH sensing

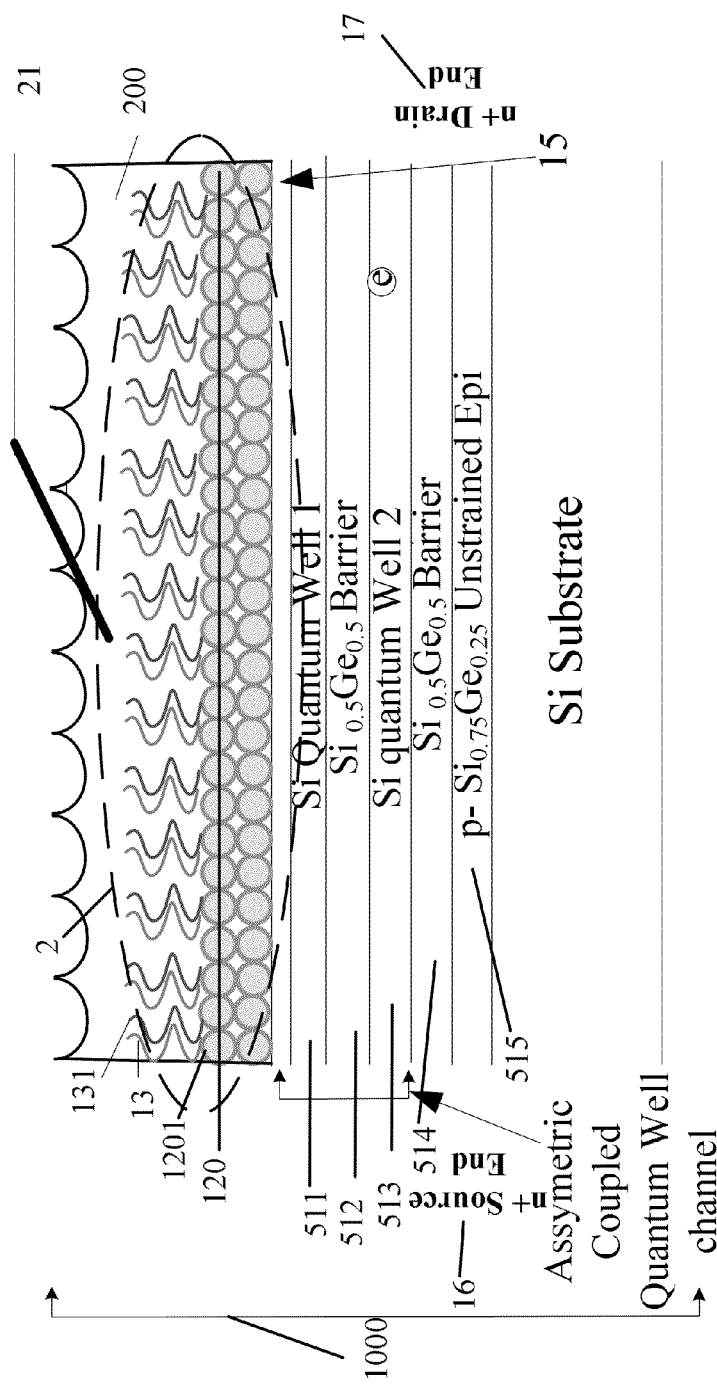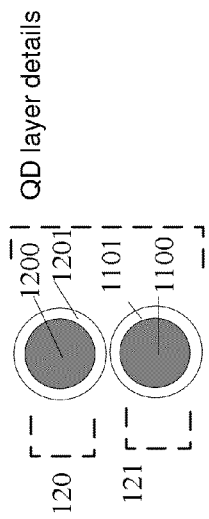
FIG. 9A
Quantum dot gate SWS FET configured as a DNA, RNA, or MicroRNA sensor and sequencer

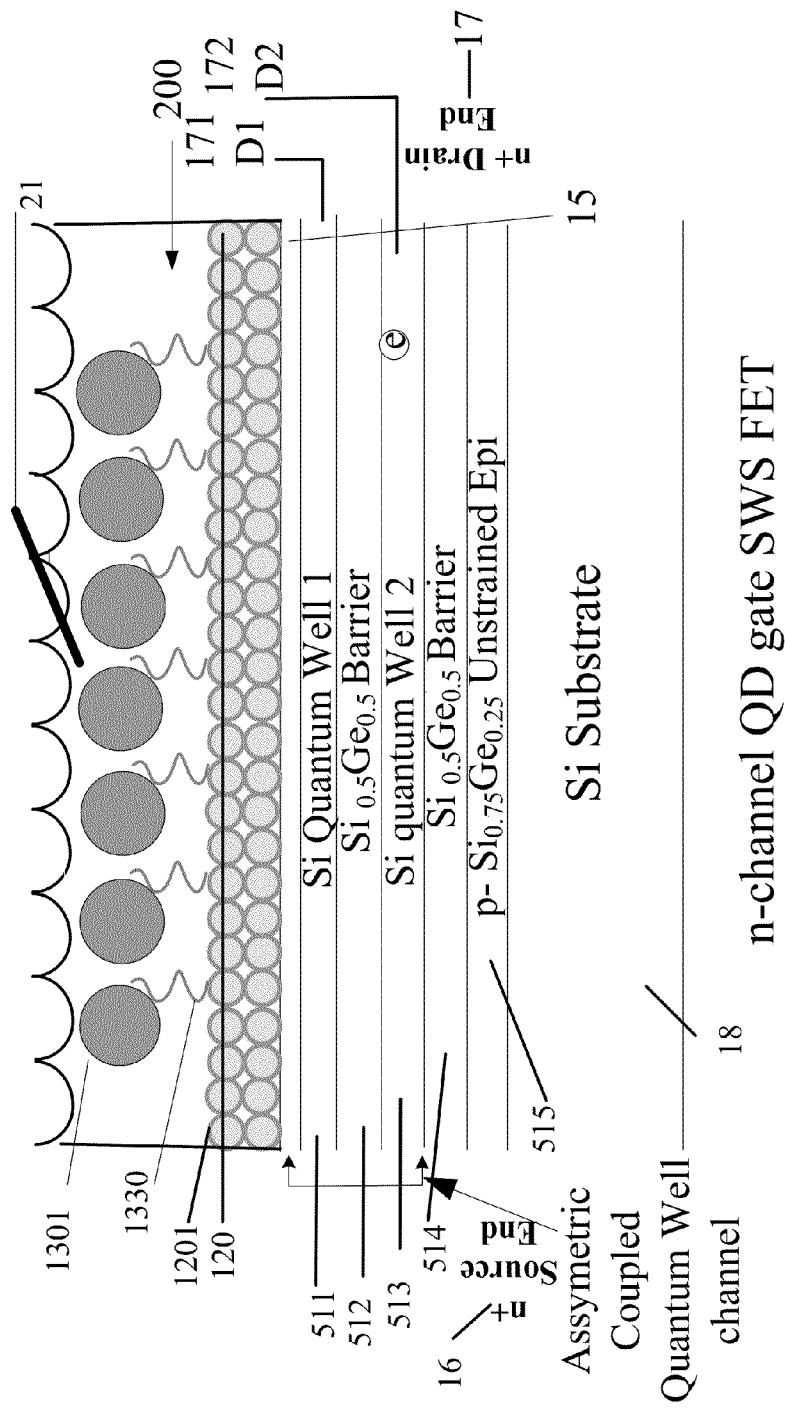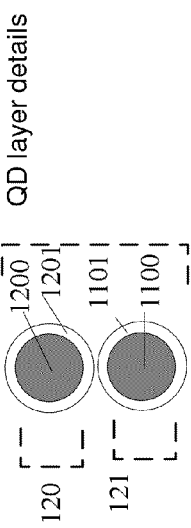
FIG. 9B
n-channel QD gate SWS FET
Quantum dot gate SWS FET configured for biomolecule sensing. Here, ssDNA aptamers sense the protein Thrombin.

Quantum dot gate SWS FET configured as a glucose sensor using glucose oxidase

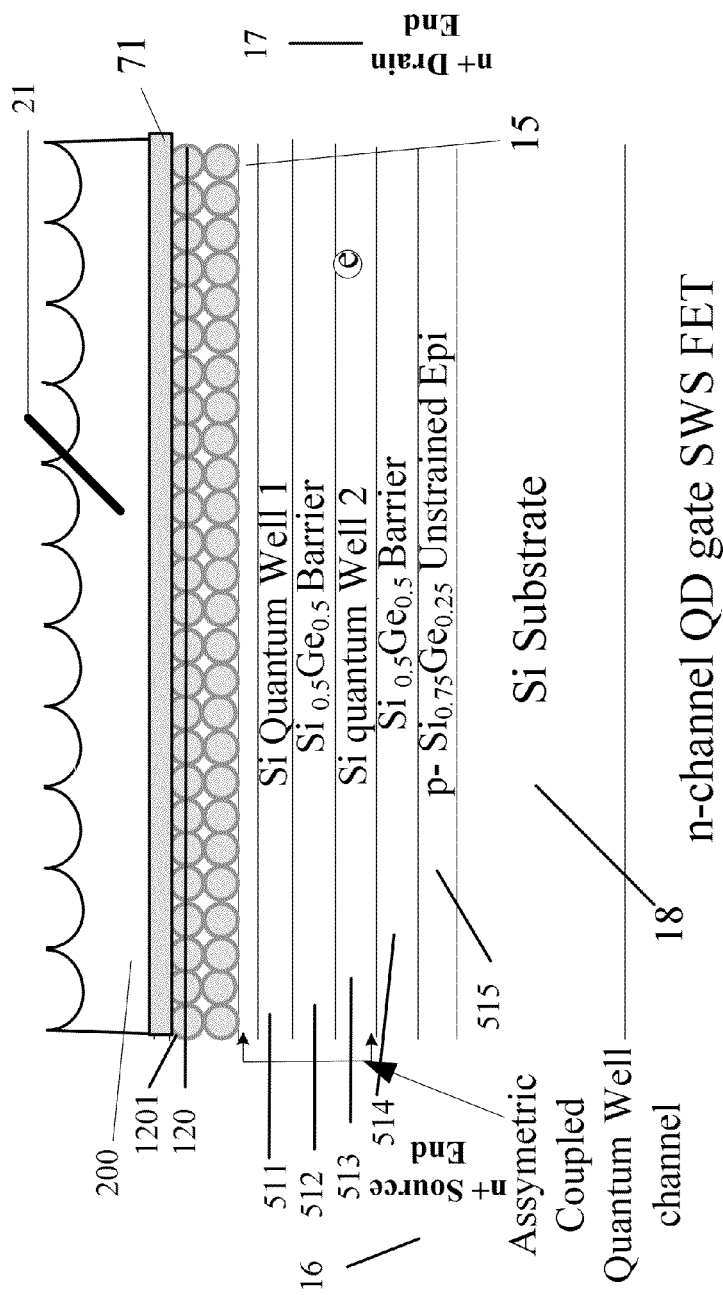
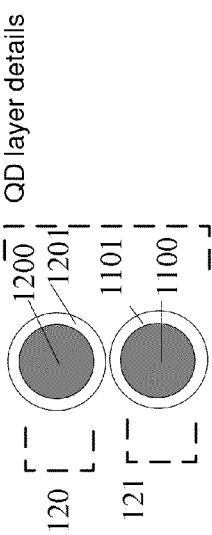
FIG. 10
Quantum dot gate SWS FET configured as a pH sensor

Array of QD-FET Sensors

DNA₁₁ DNA₂₁ ... DNA_M1
DNA₁N DNA₂N ... DNA_MN

Array of Sensors for gene sequencing

FIG. 12

QUANTUM DOT GATE FETS AND CIRCUITS CONFIGURED AS BIOSENSORS AND GENE SEQUENCERS

CROSS REFERENCE TO RELATED APPLICATIONS

This application claims the benefit of U.S. Provisional Patent Application No. 61/567,507, filed Dec. 6, 2011 and entitled "Quantum Dot Gate FETs and Circuits Configured as Bio sensors and Gene Sequencers," the contents of which are incorporated herein by reference in its entirety.

STATEMENT REGARDING FEDERALLY SPONSORED RESEARCH

The United States Government has certain rights in this invention pursuant to National Science Foundation Grant No. ECS 0622068 and Office of Naval Research Contract No. N00014-06-1-0016.

FIELD OF THE INVENTION

The present invention relates generally to Quantum Dot (QD) gate Field-Effect Transistors (FETs) and more particularly to the use of QD gate FETs as Bio sensors and Gene Sequencers.

BACKGROUND OF THE INVENTION

Referring to FIG. 1, FIG. 2, FIG. 3 and FIG. 4, DNA detection using conventional FETs is known and has typically been done by DNA functionalization to gold gated p-channel FETs via gold-thiol interactions. Moreover, conventional FETs have been used, in a variety of forms, to detect various chemicals, ions, proteins and other analytes. One such typical configuration is shown in FIG. 1, where generally these FETs are fabricated with vapor-phase grown single-walled carbon nanotubes (SWCNTs), nanowires, or organic layer (See FIG. 3) serving as the channel, in a back gate configuration (See FIG. 1 and FIG. 3). Functionalization of these nanomaterial channels allow for direct modulation of the corresponding drain current in the presence of the desired biomolecule or analyte. In addition, top gated chemFETs have been fabricated which operate by direct functionalization of the gate metal, or by removing the conventional gate material and incorporating an ion sensitive layer to detect changes in ion concentration following the chemical or biological reaction taking place. Specifically, an array of chemFETs have been used to facilitate DNA sequencing based on detection of changes in hydrogen ion concentration (pH) (See FIG. 4).

SUMMARY OF THE INVENTION

In one embodiment of the invention, the use of quantum dot gate FETs, which can be configured as nonvolatile memories or 3-state FETs, for the purpose of sensing DNAs, RNAs, proteins and other analytes is disclosed and described. It should be appreciated that analytes reaching the QDs change the gate charge and hence the current-voltage characteristics. In one embodiment, DNA sensing may be accomplished by binding a complementary DNA strand target to an existing reference DNA functionalized (i.e. attached to the QD surface by either direct covalent/binding, or immobilized in a polymer/organic matrix) onto quantum dots which are located in the gate region of the FET. The complementary DNA strand target attaches to the reference DNA and produces a change in the signal current of the FET. Protein sensing is done by their binding to antibodies or DNA aptamers, which are functionalized to the QDs prior to sensing.

Accordingly, the invention involves the use of quantum dot gate FETs for analyte, protein, DNA, sensing, RNA sensing and gene sequencing. Here, the quantum dots are placed in the gate region. Depending on the construction, the QD gate FET can be configured as a regular FET, a 3-state FET, or a non-volatile memory. In one embodiment, (See FIG. 5) cladded QDs, which may be selected from at least one of $SiO_x$-cladded-Si, $GeO_x$-cladded-Ge, ZnSe-cladded-Ge, ZnS-cladded-Si, etc., are self-assembled or deposited on a thin layer of gate insulator between the source and drain regions. The QD cladding layer and core thicknesses are such that they permit charge transfer and influence the inversion channel between the source and drain. For example, thinly SiOx cladded (~1 nm) Si quantum dots (3-5 nm diameter) permit tunneling of electrons from either one quantum dot layer to the other or from the inversion transport channel to the quantum dot layer via the tunnel oxide gate insulator ($SiO_2$) over pSi substrate between the source and drain contacts. It should be appreciated that other thicknesses can be used as desired.

When used as a biosensor, QDs are either coated with a polymer/organic film, in which enzymes such as glucose or lactate oxidase are immobilized (for redox based detection) or functionalized using silane chemistry such that appropriate functional groups coat the QD cladding surface which serves as a platform for further binding of recognition species. In fact, depending on the application, a wide variety of recognition elements can be covalently attached to the silane functionalized QDs which serve as a detection site for the desired biomolecule. The recognition element employed is a biomolecule which specifically binds to the target of interest. Such recognition elements are comprised of antibodies, DNA/RNA aptamers and various enzymes. Additionally, without the use of a recognition element, ions have the capability of being detected by passing through a semi-permeable membrane, altering the local pH or conductivity of the electrolyte. In the case of redox-based sensing, for example, glucose oxidase can be polymerized on the surface of the QDs, which in the presence of glucose, produces a measurable signal via $H_2O_2$ oxidation in the presence of the correct gate potential.

It should be appreciated that Functionalization typically means changing the outer molecular arrangement of the quantum dots. For example, OH termination on quantum dots after functionalization becomes COOH (carboxyl group) which can bind easily with amine groups. The end termination in DNA aptamers bind to QDots on one hand and become receptors to a specific protein molecule (that we would like to detect). Aptamers are synthetic oligonucleotides that can be synthesized in-vitro to bind a wide variety of proteins, drugs, small molecules and viruses. Binding to these species takes place by the aptamer folding into tertiary structures, similar to antibody-antigen binding. Aptamer binding can also take place through combination of Van der Waals forces, hydrogen bonding and electrostatic interactions.

In another embodiment of the invention, DNA, RNA, and/or microRNA (miRNA) sensing may be done with the functionalization of a known reference nucleotide sequence onto quantum dots which are located in the gate region of the FET. In this case, the target complementary oligonucleotide strand attaches to the reference oligonucleotide and produces a change in the signal current of the FET. It should be appreciated that the terms "oligonucleotide" and "oligo" are used herein interchangeably.

In still yet another oligo-based embodiment, DNA or RNA aptamer strands specific to a certain protein may be functionalized on a QD surface, followed by a specific protein attachment. One example includes the thrombin aptamer-thrombin system. This condition changes the gate charge, which in turn is detected by the change in current in the FET channel.

In still yet another oligo-based embodiment, a matrix of QD FETs may be used, where various FET gates are functionalized with DNA strands having different base sequencing. In this case, flowing an appropriate solution(s) containing target genes, using a network of microfluidic channels, on top of gates will enable detection of complementary DNA strands or enable gene sequencing. Antibodies can also be immobilized to the QDs for detection of the antigen present in the solution.

In still yet another embodiment, Spatial Wavefunction-Switched (SWS) channel based QD gate FETs may be used where detection could be channel location dependent via the use of twin-channel FETs. Moreover, detection of miRNAs is significant in the diagnosis of traumatic brain injury and other neural disorders as well as classification of cancer. Accordingly, in still yet another embodiment, miRNAs can be detected subcutaneously with the provision of refreshing the binding sites using light/laser assisted localized heating which enables detachment of bases. It should be appreciated that the sensed signal from various devices, as disclosed herein, can be retrieved by signal processing and optical transmission, as described in U.S. patent application Ser. No. 11/862,866 to Jain, et al. the contents of which are incorporated herein by reference.

BRIEF DESCRIPTION OF THE DRAWINGS

The foregoing and other features and advantages of the present invention will be better understood from the following detailed description of illustrative embodiments, taken in conjunction with the accompanying drawings in which:

FIG. 9A is a cross-sectional schematic of quantum dot gate spatial wavefunction switched (SWS) FET 1000 for DNA, RNA, and MicroRNA sensing and sequencing, in accordance with a fifth embodiment of the invention.

FIG. 9B is a cross-sectional schematic of a quantum dot gate SWS FET for the sensing of biomolecules, in accordance with a sixth embodiment of the invention.

FIG. 10 is a cross-section schematic of a quantum dot gate SWS FET for pH sensing, in accordance with an eighth embodiment of the invention.

FIG. 12 is schematic block diagram illustrating an array of sensors for gene sequencing is shown, in accordance with a tenth embodiment of the invention.

DETAILED DESCRIPTION OF THE INVENTION

It should be appreciated that CNT FETs and nanowire sensors are prone to threshold fluctuations which result in current changes from sensor to sensor. Moreover, current electronic gene sequencers are based on H+ proton production when base pairs on reference DNA strands match/bond with unknown target DNA strand. The H+ concentration changes the pH which is read and correlated. In the present invention, the release of H+ protons when reference DNA strands bond with unknown target DNA strand (due to base pair conjugation), the DNA charge is altered. This in turn changes the Quantum Dot charge. Moreover, in the present invention, for protein sensing, the protein binds to a DNA aptamer and changes the charge in the gate region. This directly affects the FET drain current.

It should be appreciated that the present invention involves the use of quantum dot (QD) gate field-effect transistors (FETs), which are generally used as nonvolatile memories and 3-state FETs in electronic circuits, for the purpose of sensing various chemicals, ions, and bio-molecules in a label-free affinity type or redox configuration. These species include, but are not limited to, analytes (such as glucose), a wide range of diverse proteins, antigens, and DNA or RNA strands. These species, which are bound to their recognition element that is functionalized to the QDs, have a direct effect on the charge density in the gate region of the FET. This effect can be quantified by observing the change in the current-voltage characteristics of the FET as different concentrations of these species are immobilized. As described further herein, in one embodiment, DNA sensing is carried out by its binding to an existing complementary DNA strand functionalized onto the quantum dots located in the gate region. This is in contrast to conventional FET-based DNA detection, which is done by DNA functionalization to gold gated p-channel FETs via gold-thiol interactions.

The use of quantum dot gate FETs, which can be configured as nonvolatile memories or 3-state FETs, for the purpose of sensing analytes, DNAs, RNAs and proteins is disclosed and described herein. It should be appreciated that analytes reaching the QDs change the gate charge and hence the current-voltage characteristics. In one embodiment DNA sensing is done by its binding to an existing reference DNA functionalized onto quantum dots which are located in the gate region of the FET. The complementary DNA strand target attaches to the reference DNA and produces a change in the signal current of the FET. Protein sensing may be done by their binding to antibodies or DNA aptamers, which are functionalized to the QDs prior to sensing.

Figure 1:
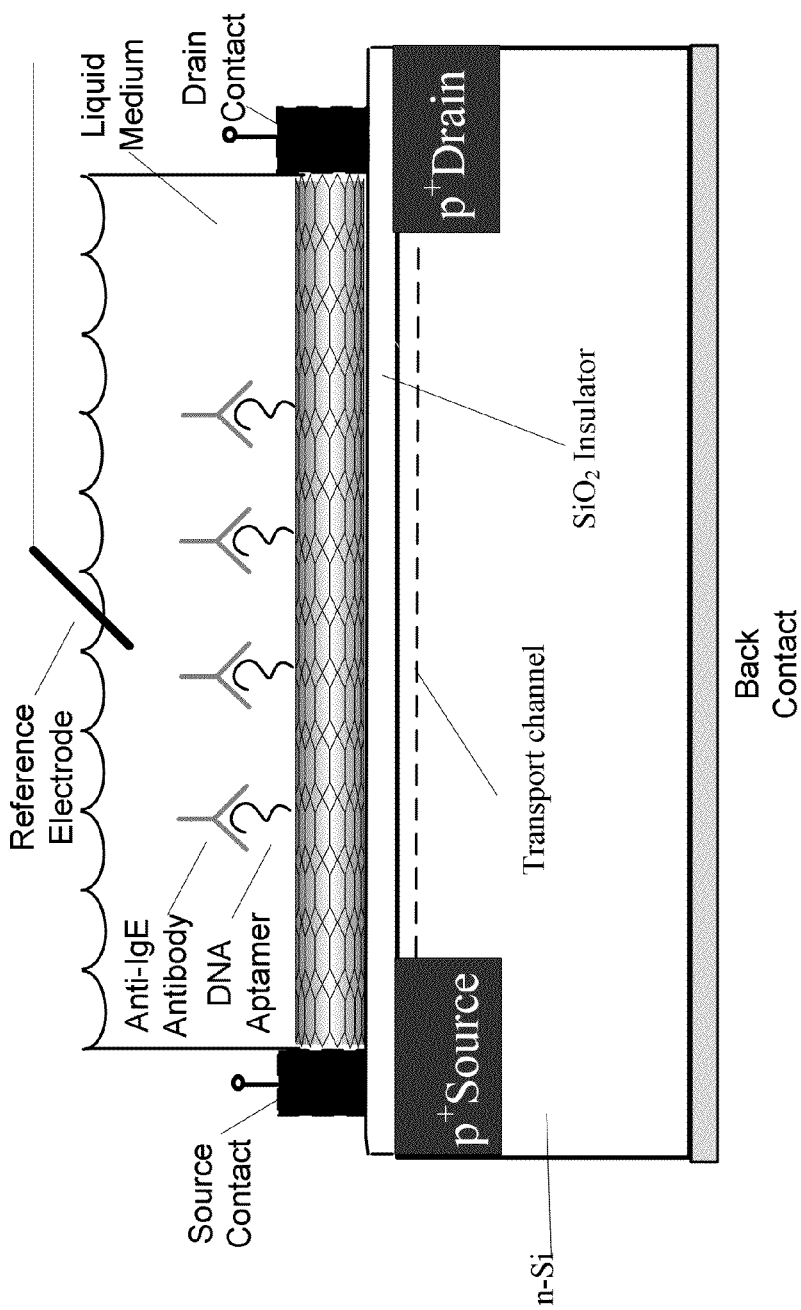
FIG. 1 is a schematic cross-section of a SWCNT-FET configured for use as an affinity-type biosensor, in accordance with the prior art.

Referring to FIG. 1, a cross-sectional schematic of a SWCNT-FET employed as an affinity-type bio sensor is shown in accordance with the prior art. The SWCNT 100 is processed on top a thermally grown oxide to span the channel between the source and drain in a back gate configuration utilizing a back contact on an n-type substrate. Biomolecules such as antibodies, DNA or RNA aptamers, enzymes, etc., can be directly immobilized to the SWCNT, enabling direct modulation of the device drain current. In this case, an IgE DNA aptamer, specific to the immunoglobulin E (IgE) antibody, is functionalized to the SWCNT surface via surface modification of the SWCNT which serves as a linker. This sensing scheme enables direct modification of the current flowing through the SWCNT channel as various concentrations of IgE is present on the SWCNT.

Figure 2:
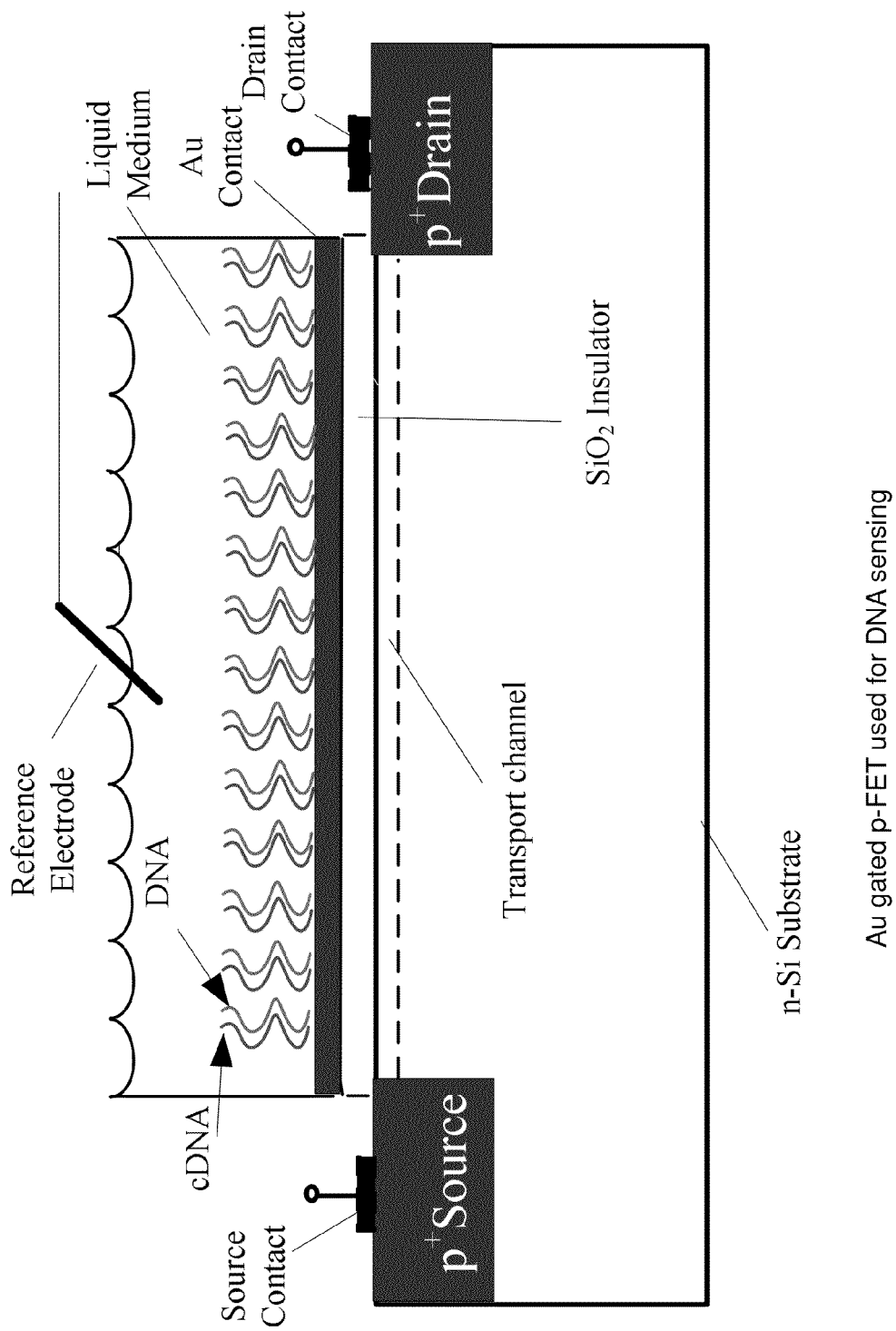
FIG. 2 is a schematic cross-section of a liquid top-gated FET configured for use for DNA or RNA sensing, in accordance with the prior art.

Referring to FIG. 2, a cross-sectional schematic of a liquid top-gated FET used for DNA or RNA sensing, and gene sequencing realized on an n-type substrate is shown in accordance with the prior art. Thiol modified DNA or RNA strands are immobilized to the gold gate electrode by means of the unique gold-thiol interaction. The gold electrode is deposited on top of a thermally grown gate oxide in the gate region spanning the p-type source and p-type drain. Source contacts and drain contacts are formed to bias the FET sensor. Gate voltage is applied to the liquid gate by means of a reference electrode such as Ag/AgCl. Hybridization is then carried out by passing complementary DNA or RNA strands over the reference strands.

Figure 3:
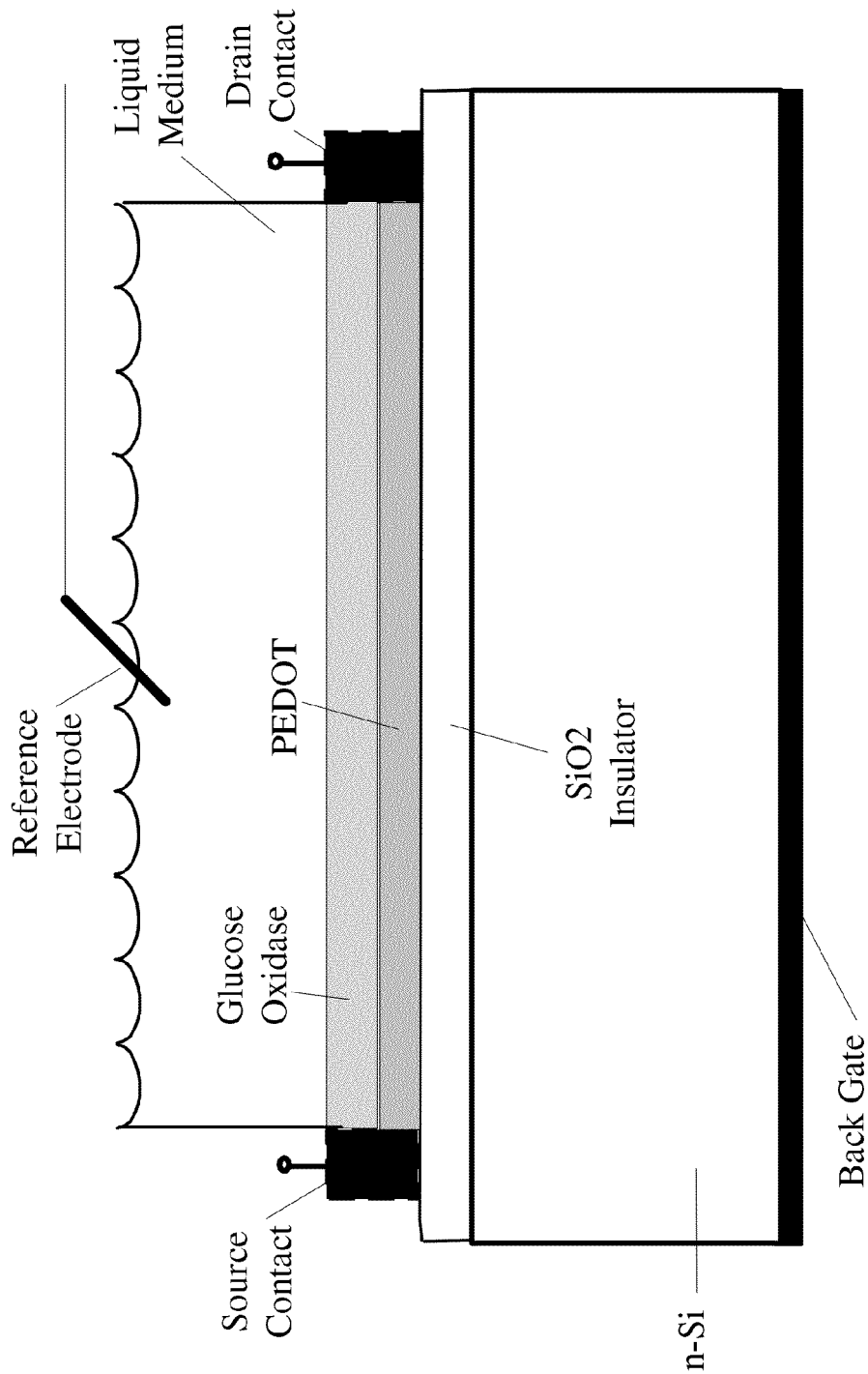
FIG. 3 is a schematic cross-section of a redox-based glucose sensor, in accordance with the prior art.

Referring to FIG. 3, a cross-sectional schematic of a redox-based glucose sensor is shown in accordance with the prior art. This device works on the principle of the oxidation of $H_2O_2$, which is a byproduct of the reaction of glucose with glucose oxidase, and transfers electrons to the PEDOT channel which sits on top a thermally grown oxide layer. Source contact drain contact and back contact is used to bias the device, which is processed on an n-type substrate.

Figure 4:
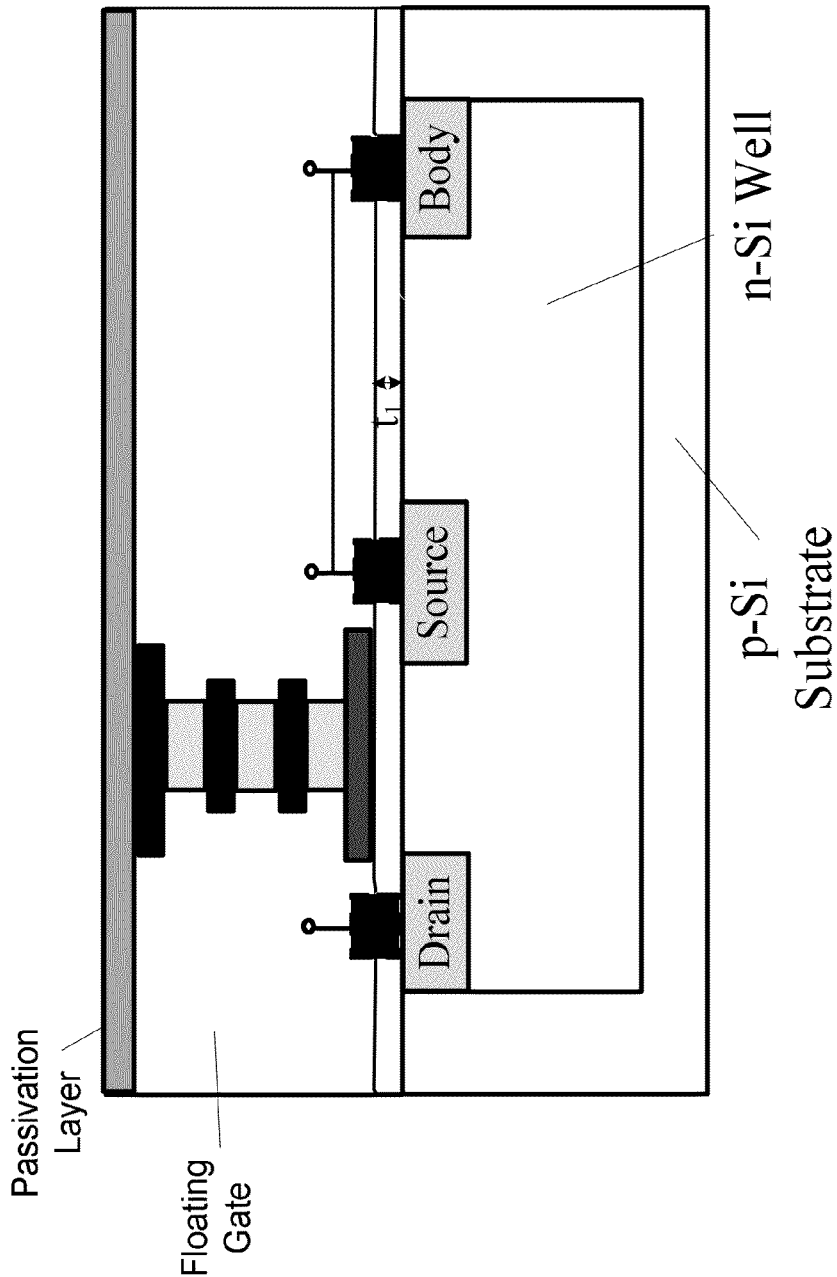
FIG. 4 is a schematic cross-section of a pH sensitive ion sensitive field effect transistor (ISFET) configured to be used for the detection of DNA sensing and synthesis, in accordance with the prior art.

Referring to FIG. 4, a cross-sectional schematic of a pH sensitive ion sensitive field effect transistor (ISFET) used for the detection of DNA sensing and synthesis is shown in accordance with the prior art. The scheme here is based on hydrogen ion sensing, as protons are released into the solution when two complementary strands are hybridized. This increase in proton concentration directly affects the pH of the solution which can be measured using the ISFET.

Figure 5:
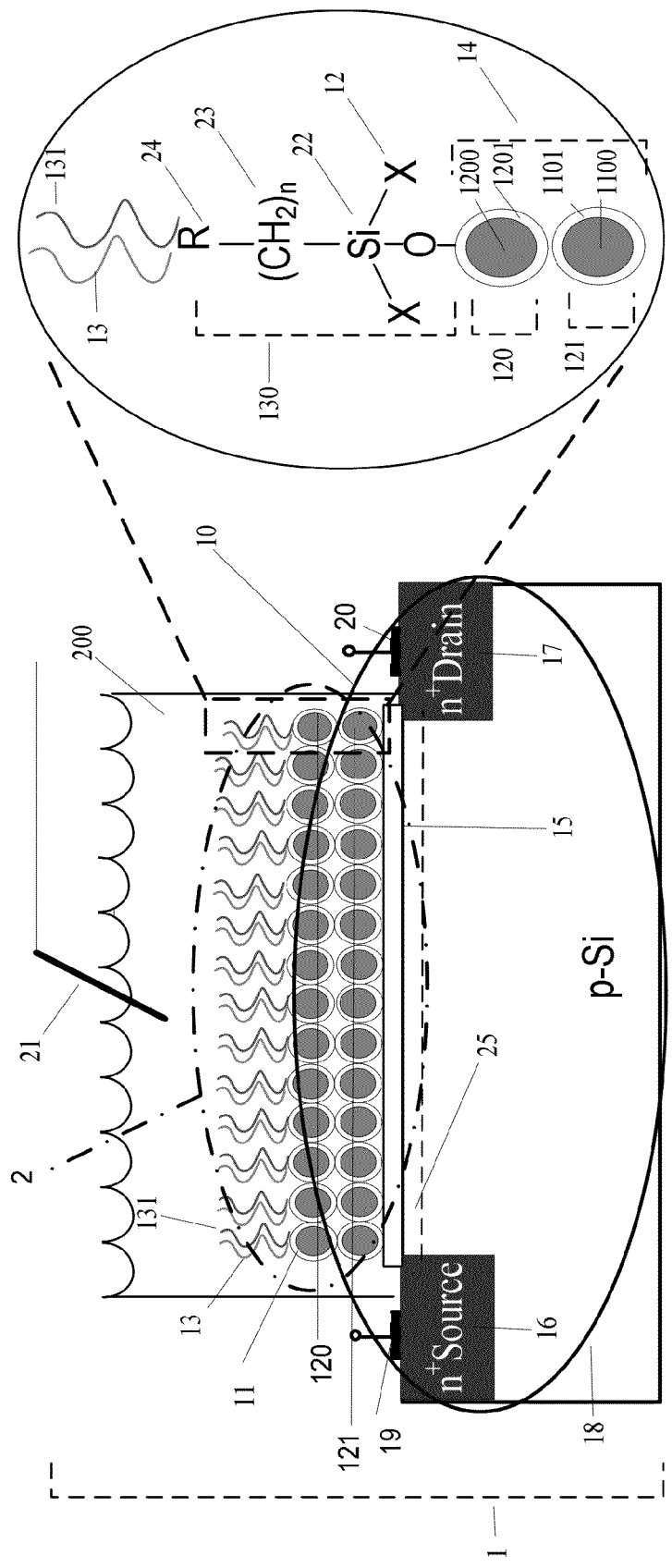
FIG. 5 is a cross-sectional schematic of a quantum dot FET sensor, in accordance with one embodiment of the invention

Referring to FIG. 5, a cross-sectional schematic of a quantum dot FET sensor 1 which includes a quantum dot gate FET 10, is shown in accordance with one embodiment of the invention. The sensor 1 is used for DNA, RNA, and/or MicroRNA sensing and sequencing. The FET 10 includes a source 16 and a drain 17 realized on a Si substrate 18. The FET gate includes two layers of cladded quantum dots 14 which are deposited on a gate insulator layer 15. The top quantum dot layer 120 and bottom quantum dot layer 110 have cladding and cores, where the cladding of the top layer 120 is labeled as 1201 and the core is labeled as 1200. Similarly, the cladding of bottom QD layer 121 is labeled as 1101 and the core is labeled as 1100. The $SiO_x$ cladding layer 1201 of the top quantum dot layer 120 serves as the functionalization site of the reference DNA 131. Cladded quantum dot layers 14 are deposited on the gate oxide layer 15 in the gate region 2 between the source 16 and the drain 17. The source 16 and drain 17 and the gate region 2 may be realized on a p-type silicon substrate 18. Source contact 19 and drain contact 20 are formed to bias the FET sensor 1 in order to induce a transport channel 25. The gate region 2 is biased by an electrode 21, where the gate electrode is immersed in an electrolyte 200. In an additional embodiment, cladded quantum nanorod layers are also contemplated and can be used.

It should be appreciated that in one embodiment two layers of cladded dots could be selected from ZnS—CdSe, ZnMgCdSe—CdS and/or AlGaN—GaN. In another embodiment more than 2 layers of $SiO_x$—Si and $GeO_x$—Ge could be used and are envisioned. In still yet another embodiment two or more layers of mixed SiOx-Si and GeOx-Ge dots are used to realize a Quantum dot gate FET where the outer layer of dots are functionalized. In terms of FETs, the p-type substrate material 18 could be selected from Si-on-insulator, Ge-on-insulator, GaN on sapphire, and/or GaN on Si. It is contemplated that other semiconductor combinations could be used and are envisioned. The use of HfO2, ZnS—ZnMgS—ZnS as a thin gate insulator (15) is also envisioned in an embodiment. Moreover, the metal oxide semiconductor (MOS) FET could be replaced by Modulation Doped (MOD)-FET structures. Here, in MODFETs QDs may be self-assembled on top of the supply layer.

The inset in FIG. 5 shows the silane modification of the cladding $SiO_x$ layer 1201 to introduce the appropriate functional group 130 onto the surface which covalently links to the reference DNA 131, RNA, or MicroRNA (which has the correct chemically modification). The silane consists of 1-3 hydrolyzable reactive groups 12, a silicon atom 22, a linker group 23 (in some cases, no linker) and a functional group 24. The hydrolysis of the reactive groups 12 first takes place, followed by condensation, then hydrogen bonding to the hydroxyl terminated cladding layer 1201. In the case where DNA has one strand 13, the addition of a complementary strand 13 to a reference strand 131, in the appropriate conditions, will induce hybridization which can be detected by a change in the source-drain current of the quantum dot FET sensor 1. Quantum dots can be terminated with the desired function group by a variety of motifs, including covalent bonding as well as ionic bonding with the positively charged quantum dots. Other suitable methods may be used as well. It should be appreciated that Hydrolyzable groups are groups that are able to react with the hydroxyl groups which are present on the quantum dot cladding oxide surface. It is contemplated that there can be one or more groups (such as one group, two groups or three groups) and are represented as "x" in the inset of FIG. 5.

Moreover, Silane deposition can be carried out in either a liquid or vapor phase method, following the standard methodology of silanization to hydroxyl terminated substrates. The silane used may be chosen such that it is terminated with the desired functional group on one end and a hydrolysable group (including but not limited to: halogen, alkoxy, amine or acyloxy) on the other. The hydrolysable group is hydrolyzed in the presence of water (which can come from the atmosphere or the substrate) to form a silanol-based species. Condensation of this species then follows, followed by hydrogen bonding with the hydroxyl groups present on the cladding layer of the quantum dots. The samples are then cured at temperatures greater than 100° C. to facilitate the removal of water and form a covalent link with the quantum dots. To obtain a monolayer of silane on the surface, it is made sure that the silane chosen contains only one hydrolyzable group in order to prevent polymerization of the silane resulting in a multi-layer deposition, or at low concentrations (0.25%) at elevated temperatures (50° C.-120° C.).

It should be appreciated that in one embodiment the gate electrode 21 may be implemented as a planar electrode in the vicinity of the source and drain. In another embodiment, the Si substrate 18 forming the FET may be replaced by a Si-on-insulator (SOI) where Si is a thin epitaxial layer in which the source, the drain and the gate regions are implemented. In FIG. 5, the passivation layer that protects the source and the drain contacts from the electrolyte is not shown. Thin films comprised of SU-8 and other photoresist materials as well as SiN and other insulators could be used as desired.

Figure 6A:
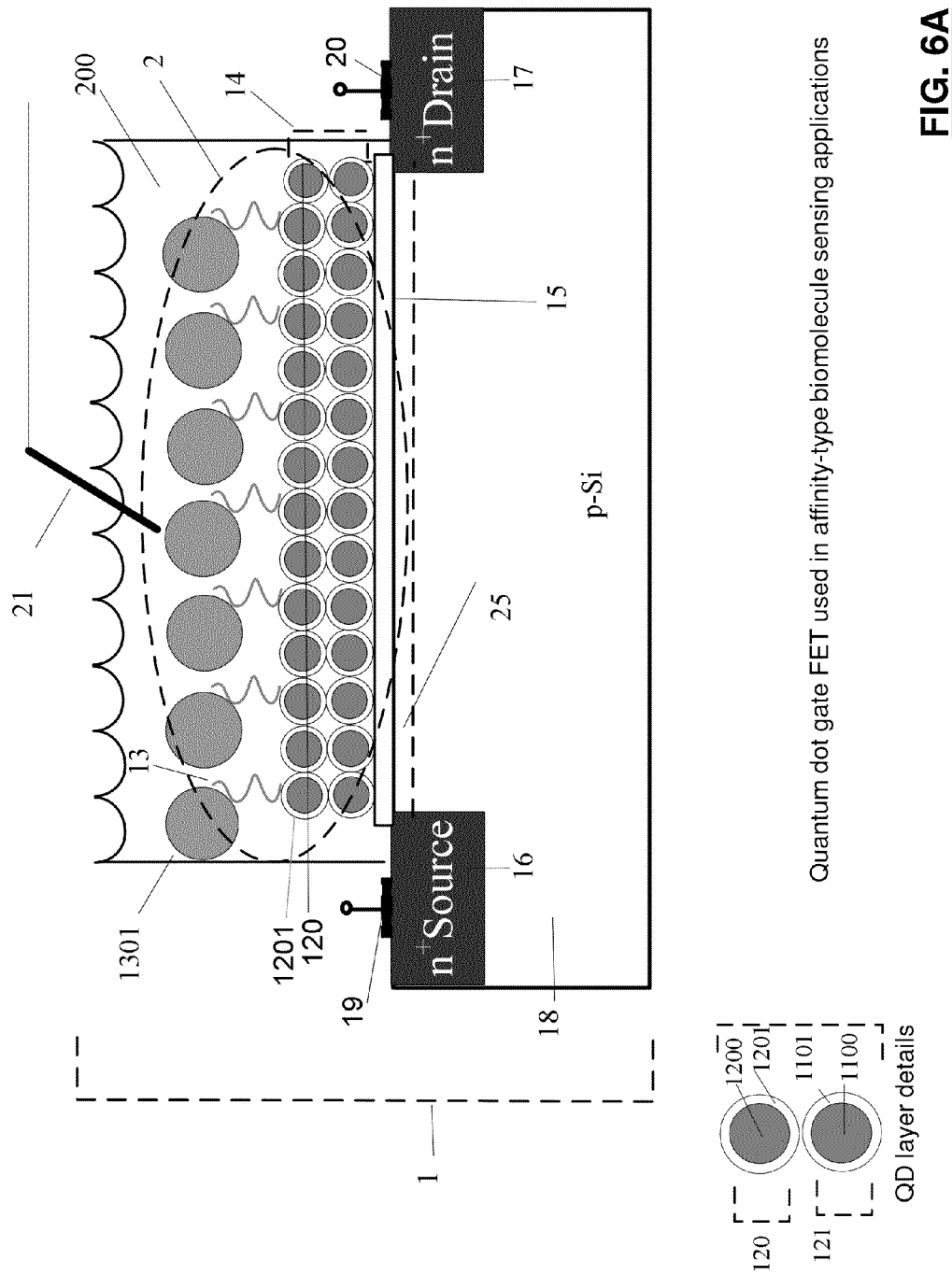
FIG. 6A is a cross-sectional schematic of a quantum dot FET sensor, in accordance with a second embodiment of the present invention.

Referring to FIG. 6A, a cross-sectional schematic of a quantum dot FET sensor 1 used for the detection of various biomolecules is shown in accordance with an embodiment of the present invention. Here, the top cladding layer 1201 of the top quantum dot layer 120 in the gate region 2 is modified with a single-stranded DNA aptamer 1300, specific to the protein Thrombin 1301. Functionalization may be carried out by first modifying the top cladding layer 1201 with the appropriate silane, which covalently links to the end of the aptamer 1300 which is terminated with the correct functional group. After functionalization, Thrombin 1301 is added to the gate 2 and detection is confirmed by a change in source-drain current of the quantum dot FET sensor 1. Source contact 19 and drain contact 20 are formed to bias the FET sensor 1. The gate region is biased by an electrode 21 in an electrolyte 200. It should be appreciated that other methods and models can be used, such as the streptavidin-biotin system or antibody-antigen interactions.

Figure 6B:
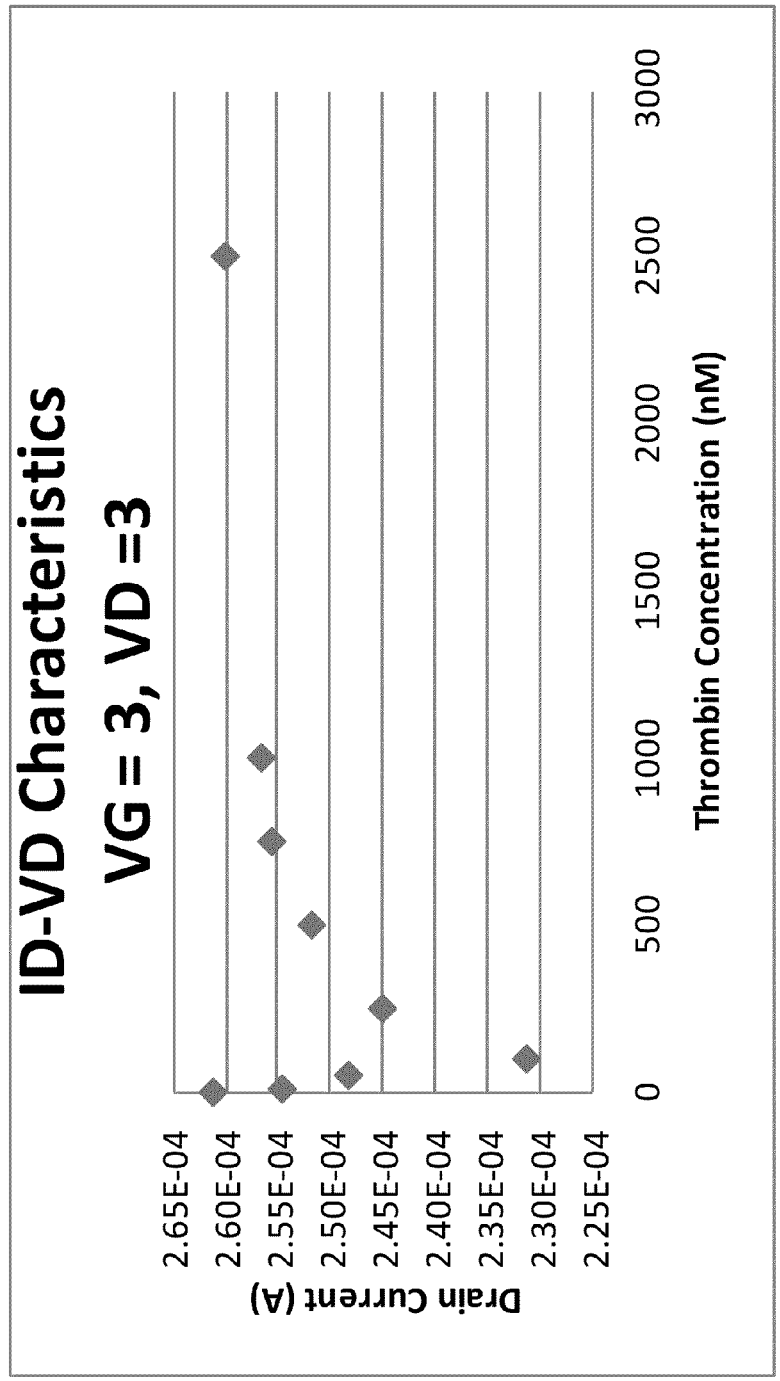
FIG. 6B is a graph illustrating the drain current-drain voltage characteristics of the device of FIG. 6A.

Referring to FIG. 6B, a graph illustrating the drain current-drain voltage characteristics of the device of FIG. 6A is shown. As can be seen, single-stranded DNA (ssDNA) aptamers specific to the protein Thrombin have been functionalized to the $Si/SiO_x$ quantum dots located in the gate region, and the drain current increases as the concentration of Thrombin increases.

Figure 7:
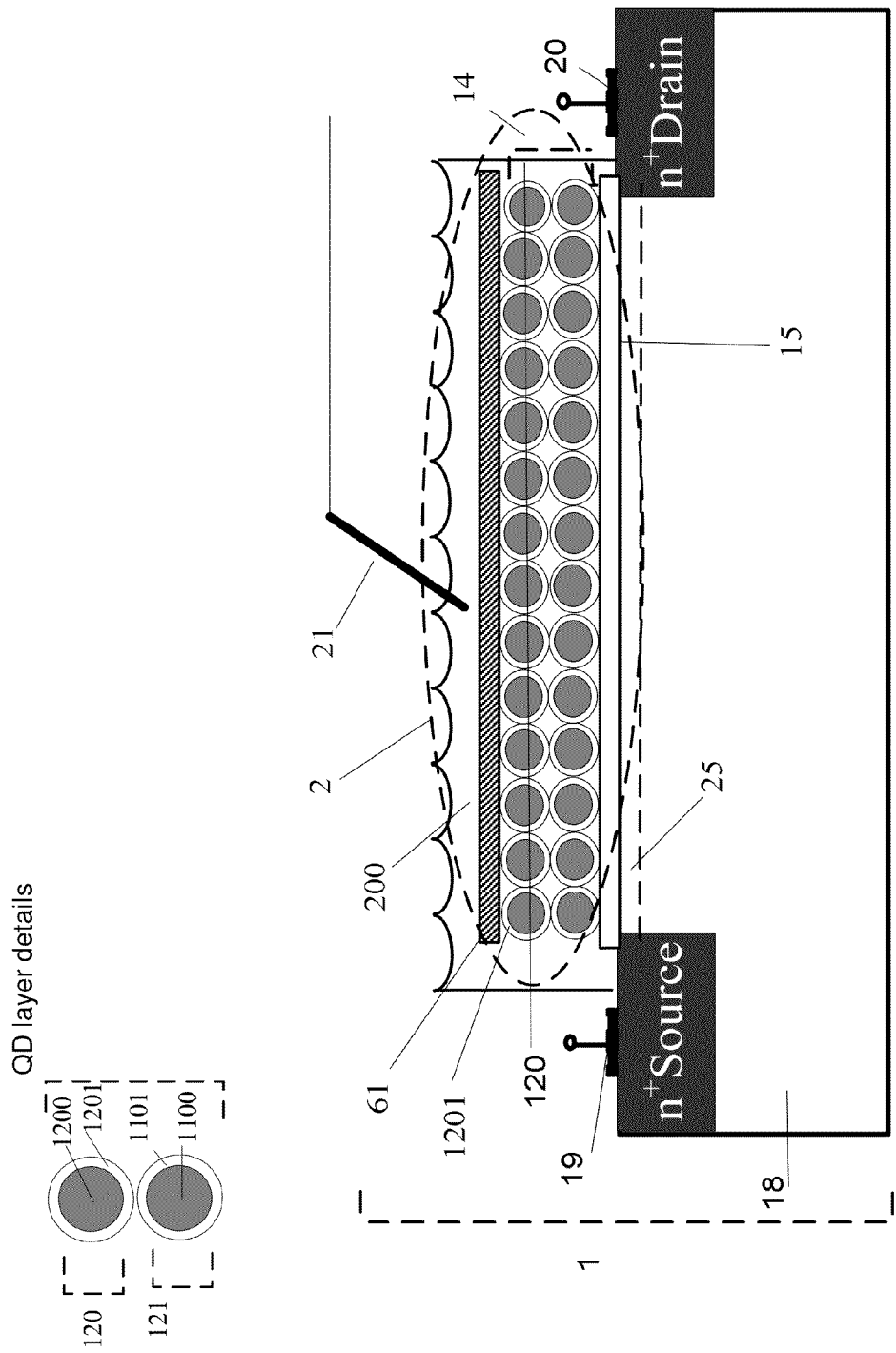
FIG. 7 is a cross-sectional schematic of a quantum dot gate FET, in accordance with a third embodiment of the invention.

Referring to FIG. 7, a cross-sectional schematic of a quantum dot gate FET 1 which is used as a redox-based sensor is shown, in accordance with one embodiment of the present invention. In this embodiment, a layer of glucose oxidase 61 coats the top layer of the quantum dots 120 in the gate region 2. This FET sensor 1 works on the principle of the oxidation of $H_2O_2$, in the presence of the appropriate oxidation potential, which is a byproduct of the reaction of glucose with glucose oxidase 61. Cladded quantum dot layers 14 are deposited on the gate oxide layer 15 in the gate region 2 between the source 16 and the drain 17. The source 16 and the drain 17 and the gate region may be realized on a p-type silicon substrate 18. The source contact 19 and drain contact 20 are formed to bias the FET sensor 1 and the gate region is biased by an electrode 21 in an electrolyte 200. It should be appreciated that, in one embodiment, the glucose oxidase layer may be deposited on a Pt electrode mesh covering the quantum dots.

Figure 8:
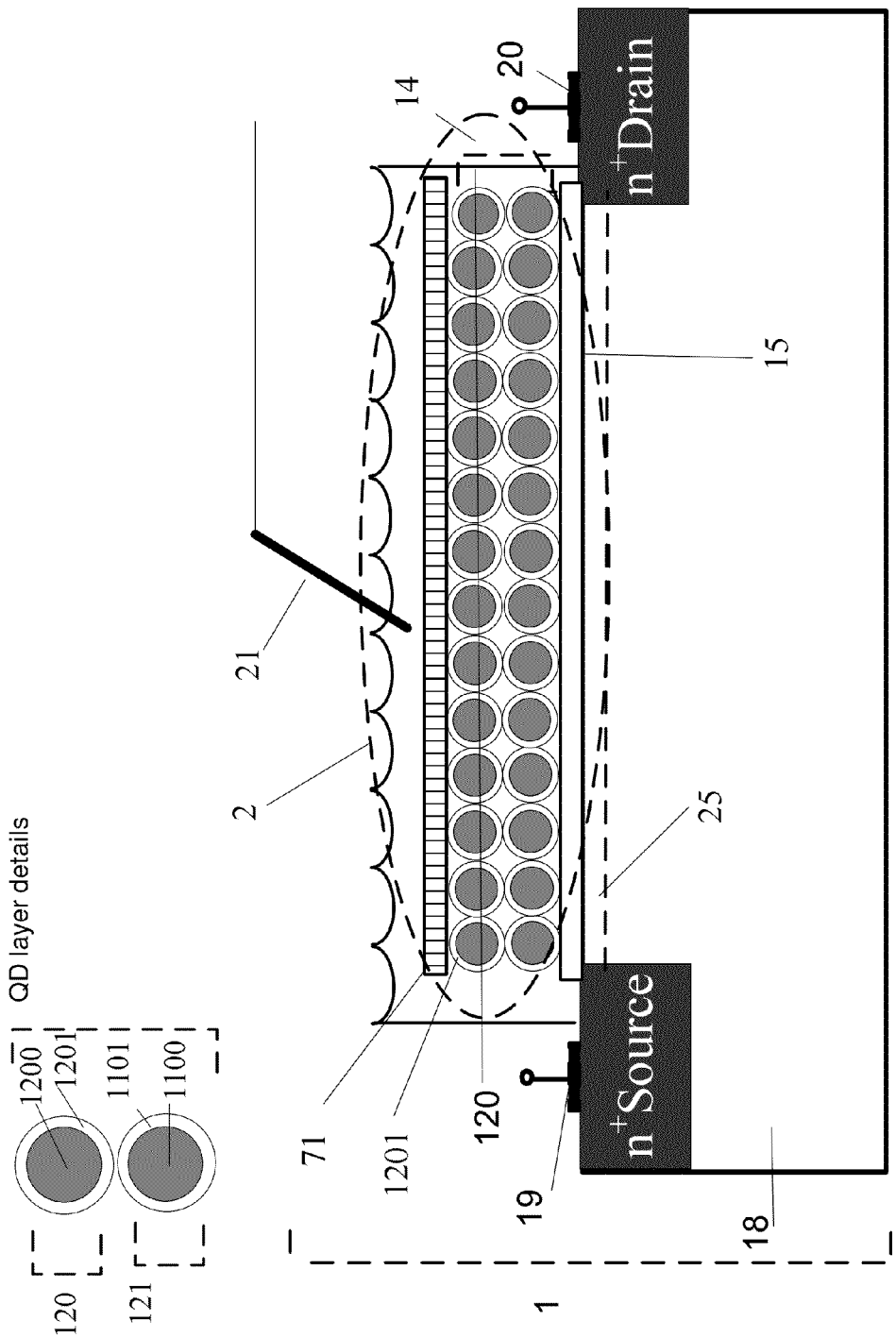
FIG. 8 is a cross-sectional schematic of a quantum dot gate FET, in accordance with a fourth embodiment of the invention.

Referring to FIG. 8, a cross-sectional schematic of a quantum dot gate FET which is used as a pH sensor is shown, in accordance with one embodiment of the present invention. In this embodiment, the top layer of quantum dots 120 are coated with a semi-permeable layer (such as SiON) 71, which permits H+ migration to the quantum dot layer. In this case, the quantum dot layer acts as a floating gate whose charge changes as the concentration of H+ changes. A change in the source-drain current occurs as the pH of the solution in the gate varies.

Referring to FIG. 9A, a quantum dot gate spatial wavefunction switched (SWS) FET 1000 for DNA, RNA, and MicroRNA sensing (detection) and sequencing is shown, in accordance with one embodiment of the present invention. In this embodiment, the FET is similar to that of FIG. 5 with the difference that the inversion channel region comprises two wells and two barriers. The top quantum well W1 is labeled as 511, which is adjoining the gate insulator 15. The other side of W1 511 is a barrier layer 512. The barrier layer 512 interfaces with a quantum well W2 513, which is interfacing with a barrier layer 514. In this embodiment, the wells W1 and W2 are Si and the barrier layers 512, 513 are Si0.5Ge0.5. The barrier layer 514 is interfacing with an unstrained Si0.75Ge0.25 layer 515. This unstrained Si0.75Ge0.25 layer 515 is grown on p-Si substrate 18. The source, drain and gate regions are same as in FIG. 5. As shown in FIG. 5, single strand DNA 13 binds with its complementary strand 131. This binding will induce hybridization which can be detected by a change in source-drain current of the quantum dot SWS FET sensor 1000. The drain current can be measured using either drain 171 (D1) or drain 172 (D2). It should be appreciated that SWS FETs have multiple drains and sources as needed. In this embodiment, two drains are shown schematically, but other drains and sources may be present.

Referring to FIG. 9B, a quantum dot gate SWS FET for the sensing of biomolecules, such as proteins 1301 is shown, in accordance with one embodiment of the present invention. Here the DNA aptamers 1330 are employed and are specific to a certain protein 1301. It should be appreciated that the level of protein present determines the FET current.

Figure 9C:
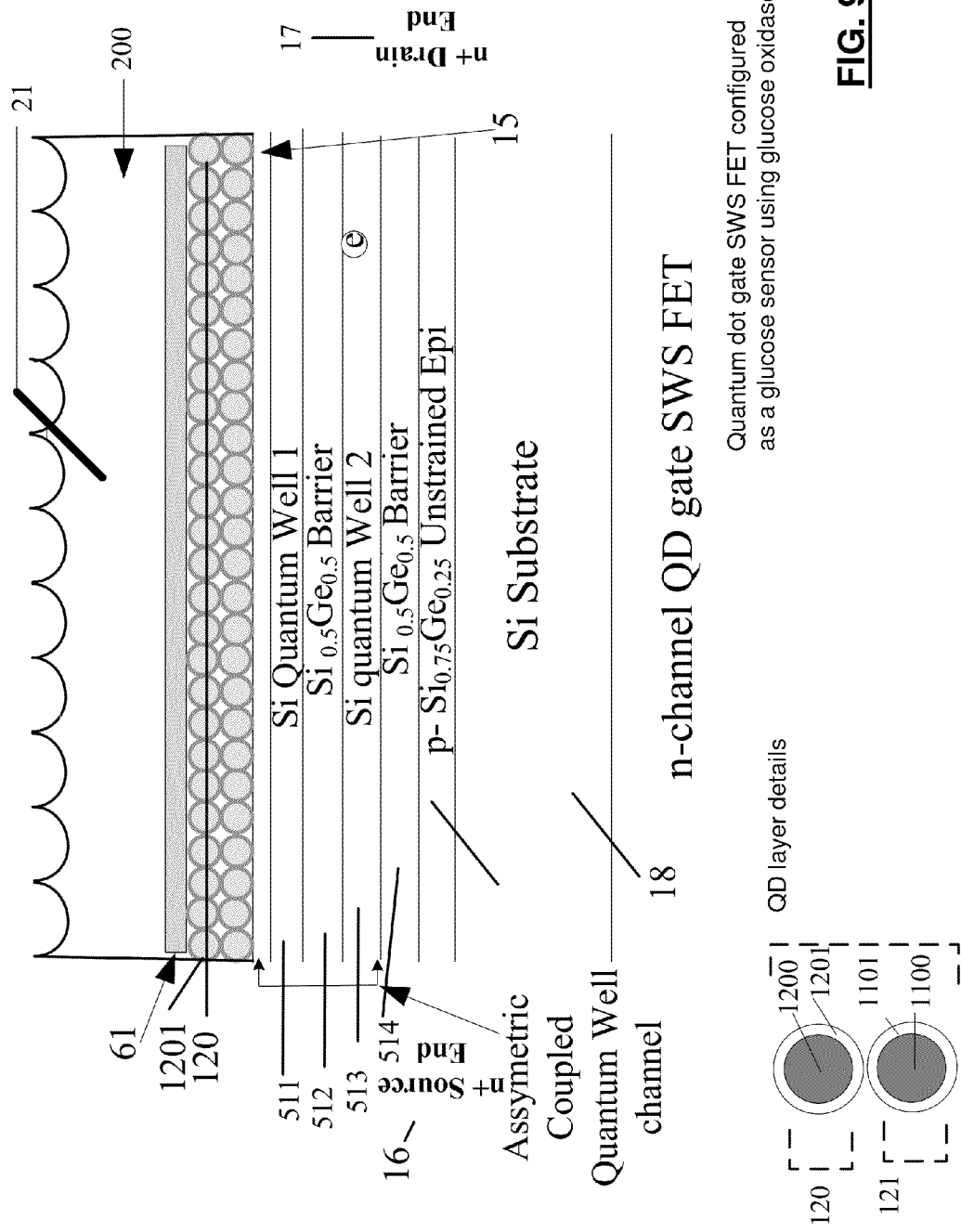
FIG. 9C is a cross-section schematic of a quantum dot gate SWS FET for redox based sensing, in accordance with a seventh embodiment of the invention.

Referring to FIG. 9C, a quantum dot gate SWS FET for redox based sensing, such as glucose detection using glucose oxidase enzyme 61 deposited on quantum dot layer 120 is shown, in accordance with one embodiment of the present invention. In this embodiment, depending on the gate voltage, the current magnitude will be different in different quantum wells. These quantum wells are connected to their respective drains as shown in FIG. 9A. It should be appreciated that more than two (2) quantum wells are also envisioned.

Referring to FIG. 10, a quantum dot gate SWS FET for pH sensing is shown, in accordance with one embodiment of the invention. In this embodiment, a layer of SiON 71 is employed, where this layer 71 permits migration of H+ protons to the quantum dot layer. It should be appreciated that other semi-permeable films could be used for this purpose.

Figure 11:
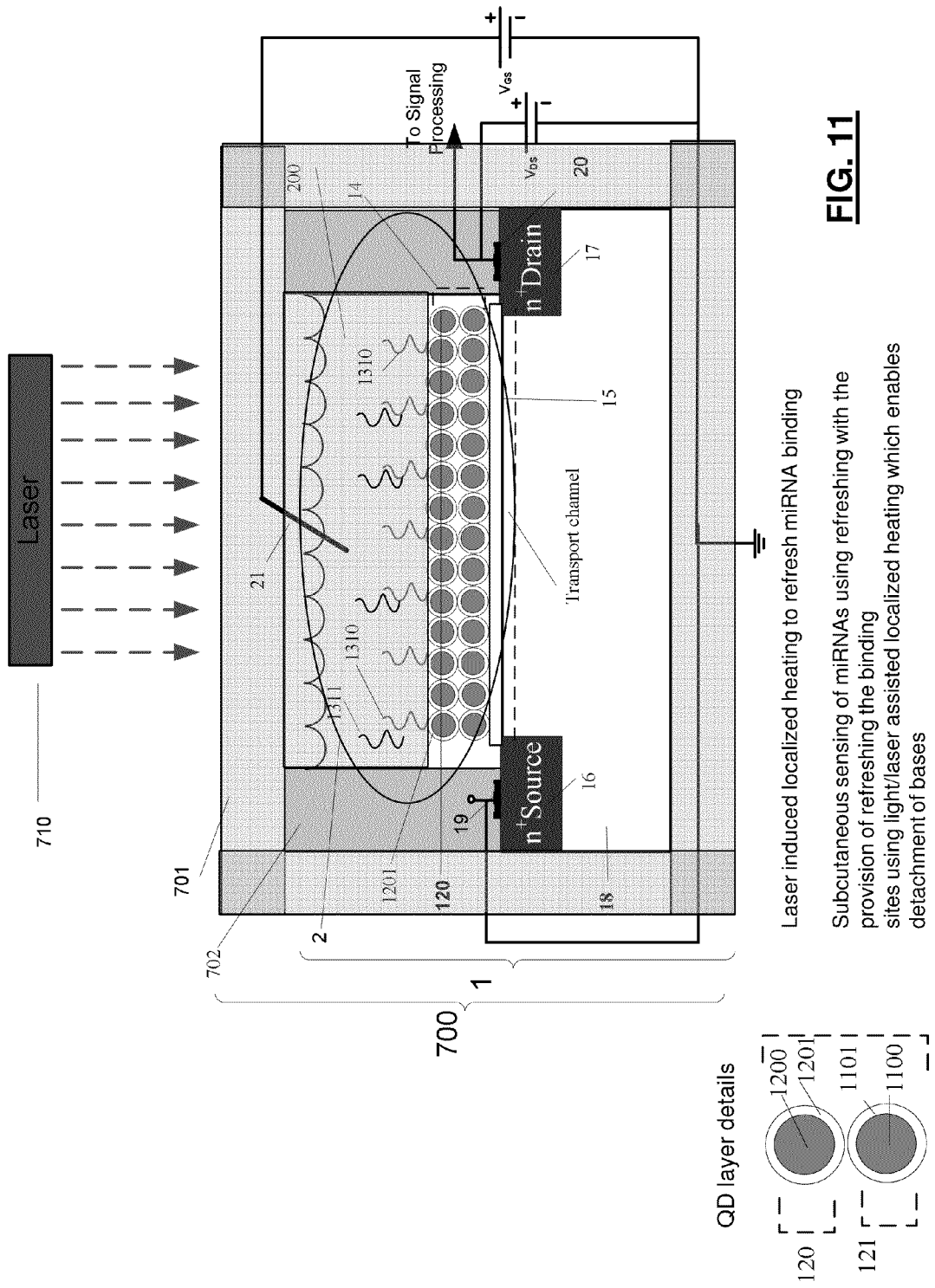
FIG. 11 is a schematic block diagram illustrating the subcutaneous sensing of miRNAs that binds to reference miRNAs, in accordance with a ninth embodiment of the invention.

Referring to FIG. 11, a schematic block diagram illustrating the subcutaneous sensing of miRNAs 1311 that binds to reference miRNAs 1310 is shown specifically here (see FIG. 5 also), in accordance with one embodiment of the invention. In this case, the binding sites are refreshed via a light/laser 710 to assist localized heating which enables detachment of the bases. The implanted device 700 has an array of quantum dot gate FET sensors 1 whose gates 2 are exposed to body fluids. The implanted device has a nanoscaffold 701 serving as a biocompatible coating, where this coating permits the flow of miRNA flux. Once the miRNAs are bonded to the target strands (which in turn functionalized to the top layer of quantum dots 120 in the gate region 2) they produce signal current which is processed by a signal processing device located on this device or on other devices that interface with this sensor 700. It should be appreciated that the source and drain contacts are passivated by a coating 702 to isolate them from the electrolyte 200. It should be appreciated that the miRNAs may be detached by localized heating that un-bonds them from a reference strand. In another method, photo assisted detachment is envisioned. In one embodiment, the heating is provided by an external light source 710 which can locally heat the Si chip. It is contemplated that other ways of heating and photo-dissociation for a short time to detach the miRNAs may be used as desired. Once the miRNAs 1311 are detached, fresh miRNAs can bond to referenced miRNAs 1310. In another embodiment, the reference miRNAs are detached from QDs and a new set could be functionalized. This set of miRNAs would now serve as reference strands 1310 and would enable detection of the next batch of unknown miRNAs. This technique could be adapted for the detection of other analytes as well.

It should be appreciated that the miRNAs are detached by localized heating that un-bonds them from the reference strand. Alternately, photo assisted detachment is envisioned. In one embodiment, the heating is provided by an external light source 710 which can locally heat the Si chip. It should be appreciated that other ways of heating and photo-dissociation for a short time to detach miRNAs may be used. Once the miRNAs 1311 are detached, fresh miRNAs can bond to the referenced miRNAs 1310. In another embodiment, the reference miRNAs are detached from QDs and a new set could be functionalized. This new set of miRNAs would now serve as reference strands 1310 and would enable detection of next batch of unknown miRNAs. It should be appreciated that this technique could be adapted for the detection of other analytes. It should be further appreciated that the present invention would benefit from a methodology to communicate with a subcutaneously implanted glucose sensor as described in U.S. patent application Ser. No. 11/862,866 to Faquir Jain entitled "Implantable Bio sensor and Methods of Use Thereof", the contents of which are incorporated by reference herein in its entirety.

Referring to FIG. 12, an array of sensors for gene sequencing is shown, in accordance with one embodiment of the invention. It is contemplated that this array of sensors could be deployed on a Si chip and each FET sensor gate functionalized to a specific target DNA, for example. If fragments of genes with different base pair combinations are used as known reference DNAs and are functionalize in the array, it is contemplated that the chip can be used to map or sequence an unknown genetic material and its coding. This is illustrated in FIG. 12. Here, the micro-fluidic channels are not shown. In still yet another embodiment, microelectromechanical (MEM) devices can be used in cooperation with microfluidic channels to control the flow of DNA, miRNA, proteins and analytes under test.

Furthermore, it should be appreciated that the following references are incorporated by reference herein in their entireties: F. C. Jain, E. Heller, S. Karmakar, J. C. Chandy, Proc. Of Int. Semiconductor Device Research Symposium (ISDRS, College Park, Md.), 2007; F. C. Jain, E. Suarez, M. Gogna, F. Alamoody, D. Butkiewicus, R. Hohner, T. Liaskas, S. Karmakar, P-Y-chan, B. Miller, J. Chandy, and E. Heller, Novel quantum dot gate FETs and nonvolatile memories using lattice-matched II-VI gate insulators, J. Electronic Materials, 38, pp. 1574-1578, 2009; S. Karmakar, E. Suarez, F. Jain, Three-state quantum dot gate FETs using ZnS—ZnMgS lattice-matched gate insulator on Si, J. Electronic Materials, 40, pp. 1749-1756, August 2011; Kim, D. S., Jeong, Y. T., Park, H. J., Shin, J. K., Choi, P., Lee, J. H., and Lim, G., "An FET-type charge sensor for highly selective detection of DNA synthesis", *Biosensors and Bioelectronics*, Vol. 20, pp. 69-74, 2004; Cid C C, Riu J, Maroto A, Rius F X, "Carbon nanotube field effect transistors for the fast and selective detection of human immunoglobulin G," *Analyst*, 2008, 133(8), 1005-8; Yoon, H., Ko, S., and Jang, J., "Field-effect transistor sensor based on enzyme functionalized glucose detection", *J. Phys. Chem. B*, 112 (32), pp. 9992-9997, 2008; Milgrew, M. J., Hammond, P. A., and Cumming, D. R. S., "The development of scalable sensor arrays using standard CMOS technology", *Sensors and Actuators: B*, Vol. 103, pp. 37-42, 2004; Pourmand, N., Karhanek, M., Persson, H., Webb, C. D., Lee, T. H., Zahradnikova, A., and Davis, W., "Direct electrical detection of DNA synthesis", *PNAS, Vol.* 103, pp. 6466-6470, 2006; F. Jain and E. Heller, Twin-drain Spatial Wavefunction Switched (SWS) FETs, U.S. Pat. No. 8,294,137, Oct. 23, 2012; F. Jain, B. Miller, E. Suarez, P.-Y. Chan, S. Karmakar, F. Al-amoody, M. Gogna, and E. Heller, "Spatial wavefunction switched (SWS) InGaAs FETs with II-VI gate insulators", J. Electronic Materials, 40, 8, pp. 1717-1726, 2011; F. Jain et al, U.S. patent application Ser. No. 11/862,866 filed in 2008 [Biosensor platform patent]; J. Bernecke, A. Stark, R. Russell, S. M. Cohen, Principles of MicroRNA-Target Recognition, PLoS Biology, Vol. 3, pp. 404-418, 2005; P. Roth, J. Wischhusen, C. Happold, P. Chandran, S. Hofer, G. Eisele, M. Weller, and A. Keller, A specific miRNA signature in the peripheral blood glioblastoma patients, J. Neurochemistry, Vol. 118, pp. 449-457, 2011; N. C. Ringger, B. E. O'Steen, J. G. Brabham, X. Silver, J. Pineda, K. K. W. Wang, R. L. Hayes, and L. Papa, A Novel Marker for Traumatic Brain Injury: CSF αII-Spectrin Breakdown Product Levels, J. Neurotrauma, Vol. 21, pp. 143-1456, 2004; and J. Lu et al., "MicroRNA expression profiles classify human cancers", Nature, Vol. 435, pp 834-838, 2005.

It should be appreciated that while the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A bio sensor device comprising:
   a field-effect transistor (FET) structure having a source, a drain, a gate region and a semiconductor substrate, wherein the semiconductor substrate includes a transport channel between the source and the drain and wherein the transport channel is configured to be controlled via a voltage applied to the gate region, and wherein the gate region includes a multilayer structure having:
      a first layer located adjacent to the transport channel, wherein the first layer is at least one of an insulator, a wide energy gap lattice matched semiconductor and a pseudomorphic semiconductor layer, wherein the multilayer structure includes at least one layer of cladded quantum dots having an outer cladding layer, wherein the at least one layer of cladded quantum dots is constructed from the group comprised of $SiO_x$-cladded Si nanocrystal quantum dots and $GeO_x$-cladded Ge nanocrystal quantum dots, wherein the outer cladding layer is functionalized with a chemical group,
      wherein the chemical group is bonded to recognition elements selected from a group comprising DNA, RNA, miRNA and antibodies, and wherein the recognition elements are bonded with target biomarkers including at least one of proteins, enzymes, and analytes; and
   a top gate electrode fixed above the outer cladding layer to be in contact with a solution containing at least one target molecule.

2. The bio sensor device of claim 1, wherein the miRNA are configured to be detached using laser assisted heating once sensing is performed.

3. A biosensor device configured as a field effect transistor (FET) structure having a 3-state behavior, the biosensor device comprising:
   a source, a drain and a gate region over a semiconductor substrate, a transport channel located between the source and the drain and under the gate region, wherein the gate region is a multilayer structure having:

a first layer, identified as a barrier layer, located adjacent the transport channel and selected from the group consisting of a thin insulator, a wide energy gap semiconductor and a lattice-matched pseudomorphic semiconductor layer, wherein the multilayer structure includes a first layer and a second layer of $SiO_x$-cladded Si nanocrystal quantum dots having an outer cladding layer, wherein the first layer and second layer of $SiO_x$-cladded Si nanocrystal quantum dots have a thin cladding of about 1-2 nm, and Si cores of about 2-8 nm, wherein the outer cladding layer of the second layer is functionalized with a chemical group, that is bonded to recognition elements constructed from at least one of DNA, RNA, miRNA and antibodies, wherein the recognition elements are bonded with target biomarkers including at least one of proteins, enzymes, DNA, RNA, miRNAs, and analytes, a top gate electrode located above the second layer in a solution containing at least one target molecule, wherein the top gate-electrode is located over the functionalized outer cladding layer of the second layer, which is configured to controls the amount of charge located in the first layer and second layer of $SiO_x$-cladded Si nanocrystal quantum dots, thereby rendering the field-effect transistor to serve as a 3-state device manifesting an intermediate state 'i' in the transfer (drain current-gate voltage) characteristic.

4. The biosensor device of claim 3, wherein the miRNA are configured to be detached using laser assisted heating once sensing is performed.

5. A field-effect transistor structure having a 3-state behavior and comprising a coupled quantum well channel in a spatial wavefunction switched configuration, comprising:

a source, a drain, and a gate region, wherein the gate region comprises a multilayer structure, a first thin layer comprising of $SiO_2$, or a wide energy gap lattice-matched semiconductor layer comprising of ZnMgS or ZnBeMgSSe of 10-100 Å in thickness, wherein the first thin layer is adjacent to a semiconductor region between the source and drain regions, wherein the multilayer structure has at least two layers of cladded quantum dots deposited on it, a top surface of the at least two layers of cladded quantum dots has a gate semiconductor or metal layer, the at least two layers of cladded quantum dots comprised of $SiO_x$-cladded Si nanocrystals, and the semiconductor region under the first thin layer comprises the coupled quantum well channel, wherein the coupled quantum well channel is comprised of a strained Si layer serving as well #1, a SiGe barrier, and second Si quantum well #2, a second barrier layer located under the Si quantum well #2 which is constructed from SiGe and on a Si substrate, wherein an outer cladding layer of one of the at least two layers of cladded quantum dots is functionalized with a chemical group bonded to recognition elements constructed from at least one of DNA, RNA, miRNA and antibodies, wherein the recognition elements are bonded with target biomarkers that include at least one of proteins, enzymes, and analytes, a top gate electrode located above the functionalized outer cladding layer in a solution containing target molecules, and a gate control electrode over the functionalized outer cladding layer, which is configured to controls the amount of charge located in the at least two layers of cladded quantum dots, thereby rendering the field-effect transistor to serve as a sensor configured to use changes in drain current-gate voltage or drain current-drain voltage characteristics.

* * * * *